United States Patent [19]
Philippe et al.

[11] Patent Number: 6,130,213
[45] Date of Patent: Oct. 10, 2000

[54] AQUEOUS DISPERSION COMPOSITION OF LIPID VESICLES BASED ON CARBAMATES WITH A CHOLESTERYL CHAIN

[75] Inventors: Michel Philippe, Wissous; Christian Blaise, Saint Mande; Jean-Thierry Simonnet, Paris, all of France

[73] Assignee: L'Oreal, Paris, France

[21] Appl. No.: 09/113,565

[22] Filed: Jul. 10, 1998

[30] Foreign Application Priority Data

Jul. 10, 1997 [FR] France .................................. 97 08801

[51] Int. Cl.⁷ .................................................. A61K 31/56
[52] U.S. Cl. .......................... 514/182; 514/844; 514/845; 514/846; 514/847; 514/848; 422/59; 552/544
[58] Field of Search ..................... 514/182, 844, 514/845, 846, 847, 848; 552/544; 424/59, 401

[56] References Cited

U.S. PATENT DOCUMENTS 4,707,453 11/1987 Wagner et al. .
5,614,503 3/1997 Chaudhary et al. .

FOREIGN PATENT DOCUMENTS

92/03464 3/1992 WIPO .
WO 93/05162 3/1993 WIPO .
WO 96/18372 6/1996 WIPO .

*Primary Examiner*—Jose' G. Dees
*Assistant Examiner*—Barbara Badio
*Attorney, Agent, or Firm*—Oblon, Spivak, McClelland, Maier & Neustadt, P.C.

[57] ABSTRACT

The invention relates to a composition, in particular a cosmetic or dermatological composition, having an aqueous dispersion of vesicles with a lipid membrane, characterized in that the lipid membrane contains at least one carbamate of following formula (I):

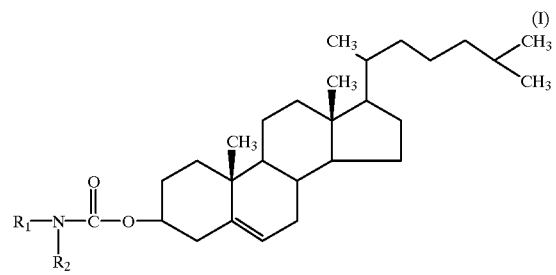

wherein $R_1$ and $R_2$ are defined in the specification.

26 Claims, No Drawings

AQUEOUS DISPERSION COMPOSITION OF LIPID VESICLES BASED ON CARBAMATES WITH A CHOLESTERYL CHAIN

BACKGROUND OF THE INVENTION

1. Field of the Invention

The present invention relates to a composition containing an aqueous dispersion of lipid vesicles based on carbamate with a cholesteryl chain and to its use in topical application.

2. Discussion of the Background

Dispersions of lipid vesicles are well known in the cosmetics field or in dermopharmaceuticals. Some amphiphilic lipids possess the property of forming mesomorphic phases, the state of organization of which is intermediate between the crystalline state and the liquid state, and some of them are capable of swelling in the presence of an aqueous solution to form a lamellar phase and, after agitation, to form vesicles or spherules dispersed in an aqueous phase. These vesicles are formed by a membrane composed of substantially concentric sheets containing one or more multimolecular layers, preferably bimolecular layers, encapsulating an aqueous phase.

Among lipids capable of forming lipid vesicles, amide compounds comprising a group derived from sugars, such as D-mannose, D-galactose and D-glucose, are known according to application WO-A-83/04412.

The above-mentioned vesicles can be prepared by numerous known processes.

According to a first process, which is described, for example, by Bangham et al. (J. Mol. Bio., 13, 1965, pages 238 to 262), the lipid phase is dissolved in a volatile solvent, and a thin film of lipid phase is formed on the walls of a flask by evaporation of the solvent. The aqueous phase to be encapsulated is then introduced to the lipid film and the mixture is agitated mechanically until a dispersion of vesicles having the desired size is obtained; an aqueous dispersion of vesicles encapsulating an aqueous phase is thus obtained. This process requires the use of a solvent during the preparation of the lipid phase.

According to a second so-called "by comelting of the lipids" process, which is described in, for example, FR-A-2,315,991, the lipid phase is prepared by mixing amphiphilic lipid(s) and optional additives at a temperature at which the mixture is molten. If the mixture is not liquid at room temperature a lamellar phase is formed by introducing the aqueous phase to be encapsulated then dispersing the lamellar phase in the form of vesicles using an ultradisperser, a homogenizer or ultrasound, in an aqueous dispersion phase. This process requires heating the lipids in order to reach their melting temperature.

To obtain dispersions of lipid vesicles which are stable over time, it is known, for example, from application EP-A-582,503, to combine, with the lipids, an additive capable of improving the encapsulation properties of the lipid membrane. Cholesterol is the additive most commonly used for this purpose. However, the preparation of these stable vesicle dispersions requires an additional stage for incorporating the additive in the lipid mixture.

Thus, the above-mentioned conventional processes require numerous stages to prepare the dispersions of lipid vesicles and these stages make the processes rather complex to employ. In addition, aqueous dispersions of vesicles are not always stable over time, depending on the lipids present in the lipid phase of the vesicles. The instability can be due, for example, to the recrystallization of certain lipids in the membrane of the vesicles or to the oxidation over time of the lipids or alternatively due to the disintegration of the structure of the lipid membrane.

It is desirable for the lipid vesicles to possess good encapsulation properties in order to make it possible to transport active ingredients according to the desired application. Thus, in addition to solving the above-mentioned problems, it is desirable to obtain lipid vesicles having good permeability.

SUMMARY OF THE INVENTION

One aim of the present invention is to provide aqueous dispersions of lipid vesicles which can be prepared according to a simpler process than those of the prior art. Another aim of the invention is to provide aqueous dispersions of vesicles exhibiting good encapsulation and stability properties.

Applicants have discovered that these and other objects of the present invention are achieved by using, as lipid, specific carbamates with a cholesteryl chain for the preparation of aqueous dispersions of lipid vesicles. It has been found that aqueous dispersions of vesicles can be prepared by simple dispersion of these lipids in water. The aqueous dispersion according to the invention is thus prepared according to a simpler process than the known processes of the prior art.

The aqueous dispersions of vesicles of the invention inhere other advantages in that they exhibit good encapsulation properties: the vesicles exhibit a low degree of leakage and are completely stable in water. In addition, the carbamates with cholesteryl chains of the invention have a high degree of swelling, which make it possible to form vesicles exhibiting a good degree of encapsulation. The aqueous dispersions of vesicles of the invention can be consequently stored and used for the preparation of compositions for topical use.

Accordingly, the first embodiment of the invention relates to a composition that includes an aqueous dispersion of vesicles having a lipid membrane, characterized in that the lipid membrane contains at least one carbamate of formula (I):

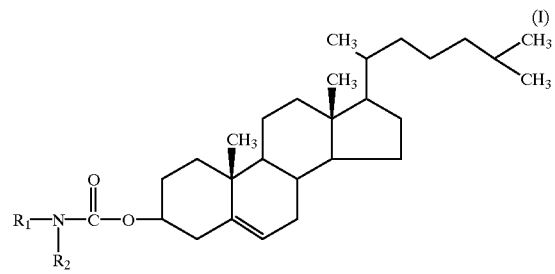

in which formula $R_1$ represents a hydrogen atom or an optionally hydroxylated, saturated or unsaturated, linear or branched alkyl radical having from 1 to 6 carbon atoms, $R_2$ represents an optionally hydroxylated, saturated or unsaturated, linear or branched alkyl radical having from 3 to 6 carbon atoms, with the proviso that the $(R_1)(R_2)N$—group contains at least two hydroxyl groups.

The second embodiment of the invention relates to a process for the non-therapeutic treatment of the skin and/or of the scalp, characterized in that a composition as defined above is applied to the skin and/or the scalp.

The third embodiment of the present invention relates to a novel compound of formula (I'):

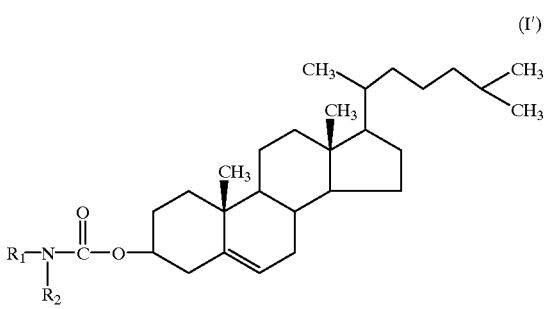

(I')

in which R₁ represents a hydrogen atom or an optionally hydroxylated, saturated or unsaturated, linear or branched alkyl radical having from 1 to 6 carbon atoms, R₂ represents an optionally hydroxylated, saturated or unsaturated, linear or branched alkyl radical having from 3 to 6 carbon atoms, with the proviso that the (R₁)(R₂)N— group contains at least two hydroxyl groups, with the exception:

of N-cholesteryloxycarbonyl-N-methyl-D-glucamine (R₁ is methyl and R₂ is the —(CH₂OH)₅—CH₂OH radical), of the compounds in which:
either R₁ represents a hydrogen atom and R₂ is a group chosen from: —CH(OH)—CH₂—CH₂—OH; —CH₂—CH(OH)—CH₂—OH; —CH(CH₂OH)—CH₂—OH; —CH₂—CH(OH)—CH₂—CH₂OH or R₁ represents an alkyl radical chosen from the group formed by the methyl, ethyl, n-propyl, isopropyl, n-butyl and t-butyl radicals and R₂ represents a group chosen from the group formed by: —CH₂—CH(OH)—CH₂—OH; —CH(CH₂OH)—CH₂—OH or R₁ and R₂ represents a —CH₂—CH₂OH radical.

The fourth embodiment of the invention relates to a process for dispersing or helping in the dispersion of a water-immiscible liquid in an aqueous phase with the carbamates of formula (I) or (I').

The fifth embodiment of the invention relates to the preparation of lipid vesicles with the carbamates of formula (I) or (I').

DESCRIPTION OF THE PREFERRED EMBODIMENTS

Various other objects, features and attendant advantages of the present invention will be more fully appreciated as the same becomes better understood from the following detailed description, which are not intended to be limiting unless otherwise specified.

Mention may in particular be made, among the compounds of formula (I), of:
N-cholesteryloxycarbonyl-N-methyl-D-glucamine,
N-cholesteryloxycarbonyl-D-glucamine,
N-cholesteryloxycarbonyl-1,1-di(hydroxymethyl) ethylamine
N-cholesteryloxycarbonyl-2,3-dihydroxypropylamine.

The compounds of formula (I) can be prepared according to processes known to a person skilled in the art. For example, these compounds can be obtained by reaction of an aminoalcohol of formula R₁—NH—R₂ with cholesteryl chloroformate, in the presence of solvent, such as N,N-dimethylacetamide.

Some of the compounds of formula (I) are described in particular in applications WO-A-91/13080, WO-A-92/03464 and EP-A-430,078, as well as in the publications Lange W. and Amundson M., Journal of Pharmaceutical Sciences, Vol. 51, No. 11 (1962), p. 1102–1106 and Reed M. et al., Journal of Medicinal Chemistry, Vol. 38, No. 22 (1995), p. 4587–4596, the entire contents of each of which are hereby incorporated by reference.

The lipid vesicles according to the invention can encapsulate an aqueous phase (lipid vesicles with an aqueous core) or an oily phase (lipid vesicles with an oily core).

The lipid vesicles with an aqueous core in accordance with the invention preferably comprise a lipid membrane formed of at least one carbamate of formula (I) and of at least one ionic amphiphilic lipid. The lipid membrane can additionally comprise at least one non-ionic amphiphilic lipid in combination with the ionic amphiphilic lipid. These lipid vesicles with an aqueous core can be prepared by any known process for the manufacture of amphiphilic lipid vesicles and more particularly according to the processes described in EP-A-504,437, the entire contents of which are hereby incorporated by reference.

The ratio by weight of the amount of carbamate of formula (I) to the amount of amphiphilic lipid is preferably between 30/1 and 50/25 more preferably 35/5 and 45/20, and the ratio by weight of the amount of lipid membrane to the amount of aqueous phase of the dispersion is preferably between 1/1000 and 300/1000, more preferably 50/1000 and 250/1000. Each of the above ranges includes all values and subranges therebetween.

The vesicles with an aqueous core in accordance with the invention advantageously have a mean diameter ranging from 10 to 1000 nm, more preferably 100 to 750 nm. These ranges include all values and subranges therebetween.

The vesicles with an aqueous core according to the invention are present in the composition in proportions preferably ranging from 0.5 to 15% and more preferably 1 to 10% by weight with respect to the total weight of the composition. These ranges include all values and subranges therebetween.

It is possible, in a known way, to incorporate, in the lipid membrane of the vesicles with an aqueous core, at least one additive, the main function of which is to decrease the permeability of the vesicles, to prevent their flocculation and their melting and to increase the degree of encapsulation. According to a preferred form of the invention, it is possible to add, to the lipid membrane, at least one additive preferably chosen from the group formed by:

sterols and in particular phytosterols and cholesterol,
long-chain alcohols and diols,
long-chain amines and their quaternary ammonium derivatives.

These additives can optionally have a cosmetic and/or dermopharmaceutical activity. This is, for example, the case with cholesterol.

The vesicles with an oily core used according to the present invention are preferably provided in the form of dispersed oily globules individually coated with a monolamellar or oligolamellar (2 to 5 lipid lamellae) layer obtained from at least one carbamate of formula (I) and from a lipophilic surfactant and/or from a hydrophilic surfactant. The monolamellar or oligolamellar layer can advantageously also comprise either an ionic amphiphilic lipid or a fatty acid, in combination with a basic agent dissolved in the aqueous phase of the dispersion.

The lipid vesicles with an oily core in accordance with the invention can be prepared according to the manufacturing process described in applications FR-A-2,709,666 and FR-A-2,725,369, the entire contents of each of which are hereby incorporated by reference. This process includes, in a first stage, mixing with agitation the fatty phase containing the fatty acid ester(s) of α-butyl glucoside, the hydrophilic or lipophilic surfactant, the ionic amphiphilic lipid or the fatty acid, and the aqueous phase and, in a second stage, subjecting the mixture thus obtained to homogenization based on the cavitation principle. This homogenization is obtained either using high pressures of between 200 and 1500 bar or using ultrasound or using homogenizers equipped with a rotor-stator head.

The lipid vesicles with an oily core as described hereinabove preferably have a mean size ranging from 10 to 500 nanometres and preferably from 20 to 200 nanometres. These ranges include all values and subranges therebetween.

The vesicles with an oily core according to the invention are present in the composition in proportions preferably ranging from 5 to 50% and more preferably 10 to 25% by weight with respect to the total weight of the composition. These ranges include all values and subranges therebetween.

The ionic amphiphilic lipids used in combination with the carbamates of formula (I) can be chosen from the group formed by:

(1) neutralized anionic lipids, these anionic lipids preferably being chosen from:
  alkaline salts of dicetyl phosphate and of dimyristyl phosphate, in particular the Na and K salts;
  alkaline salts of cholesterol sulphate, in particular the Na salt;
  alkaline salts of cholesterol phosphate, in particular the Na salt;
  salts of lipoamino acids, such as mono- and disodium acylglutamates;
  the sodium salt of phosphatidic acid;
(2) amphoteric lipids, these amphoteric lipids preferably being phospholipids, in particular pure soya phosphatidylethanolamine;
(3) alkylsulphonic derivatives, these derivatives preferably being the compounds of formula:

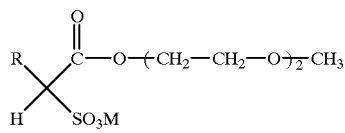

in which formula R represents $C_{12}$–$C_{22}$ radicals, in particular the $C_{16}H_{33}$ and $C_{18}H_{37}$ radicals, taken as a mixture or separately, and M is an alkali metal, preferably sodium.

The non-ionic amphiphilic lipids used for the preparation of the vesicles containing an aqueous core are preferably chosen from the group formed by:

(1) linear or branched ethers of polyglycerol of formula (II)

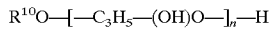

in which:
—$C_3H_5(OH)O$ is represented by the following structures, taken as a mixture or separately:

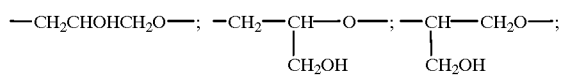

n is a mean statistical value of between 2 and 6;
$R^{10}$ represents:
  (a) a linear or branched aliphatic chain comprising from 12 to 18 carbon atoms;

(b) an $R^{11}CO$ residue, where $R^{11}$ is a linear or branched $C_{11}$–$C_{17}$ aliphatic radical;
(c) an $R^{12}$—[—$OC_2H_3(R^{13})$—]— residue, where:
  $R^{12}$ can take the meaning (a) or (b) given for $R^{10}$;
  $OC_2H_3(R^{13})$— is represented by the following structures, taken as a mixture or separately:

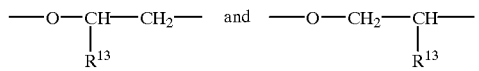

where $R^{13}$ takes the meaning (a) given for $R^{10}$;

(2) polyoxyethylenated fatty alcohols or polyoxyethylenated sterols;
(3) optionally polyoxyethylenated polyol esters;
(4) natural or synthetic glycolipids; and
(5) oxyethylenated polyglycerol stearate.

The lipophilic surface-active agents and the hydrophilic surface-active agents used for the preparation of the vesicles with an oily core preferably comprise at least one saturated fatty chain having more than approximately 12 carbon atoms. More preferably still, this fatty chain comprises from 16 to 22 carbon atoms.

According to another preferred embodiment of the invention, the lipophilic surface-active agent exhibits an HLB of between approximately 2 and approximately 5. As is well known, HLB (Hydrophilic-Lipophilic Balance) is understood to mean the balance between the size and the strength of the hydrophilic group and the size and the strength of the lipophilic group of the surface-active agent.

Examples of such lipophilic surface-active agents are sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and of palmitic and stearic acids, 2 EO polyoxyethylenated monostearate (comprising 2 oxyethylene units), glyceryl mono- and dibehenate, or pentaerythritol tetrastearate. EO represents a —$CH_2$—$CH_2$—O— unit.

The hydrophilic surface-active agent preferably exhibits an HLB of between approximately 8 and approximately 12, and more preferably approximately 9 and 11. These ranges include all values and subranges therebetween.

Mention may be made, as examples of such hydrophilic surfactants, of the following compounds: 4 EO polyoxyethylenated sorbitan monostearate, 20 EO polyoxyethylenated sorbitan tristearate, 8 EO polyoxyethylenated monostearate, hexaglyceryl monostearate, 10 EO polyoxyethylenated monostearate, 12 EO polyoxyethylenated distearate and 20 EO polyoxyethylenated methyl glucose distearate.

Depending on the value of the HLB of the carbamate or carbamates of formula (I) used for the preparation of the vesicles with an oily core, use will be made either of a lipophilic surfactant as defined hereinabove or of a hydrophilic surfactant as defined hereinabove or of the combination of a lipophilic surfactant and of a hydrophilic surfactant.

The fatty acid employed for the preparation of the vesicles with an oily core of the invention is preferably a saturated fatty acid having from 16 to 22 carbon atoms. Mention may be made, for example, of palmitic acid, stearic acid, arachidic acid and behenic acid.

Preferably, the basic agent comprised within the aqueous phase of the dispersion of vesicles with an oily core according to the invention is intended for the neutralization of the fatty acid present in the oily phase. It should most preferably be present in an amount at least equal to that necessary for the pH neutralization of all the fatty acid. It can be chosen, for example, from sodium hydroxide, triethanolamine, lysine or alternatively arginine.

The vesicles of the compositions according to the invention can contain, in a known way, one or more active compound(s) having a cosmetic and/or dermopharmaceutical activity which, depending on their solubility characteristics, can be located in different places with respect to the vesicle. If the active compounds are water-soluble, they are preferably introduced into the encapsulated aqueous phase of the vesicles with an aqueous core. If the active compounds are liposoluble, they are preferably introduced into the lipid phase constituting the membrane or else into the encapsulated oily phase of the vesicles with an oily core.

If the active compounds are amphiphilic, they are distributed between the lipid membrane and the encapsulated aqueous phase of the vesicles with an aqueous core or else between the lipid membrane and the aqueous phase of the dispersion of the vesicles with an oily core, with a partition coefficient which varies according to the nature of the amphiphilic active compound and the respective compositions of the different phases in contact with the active compound.

The water-soluble active compounds are, for example, glycerol, sorbitol, erythrulose and antibiotics. The liposoluble or partially liposoluble (amphiphilic) active compounds are chosen from those which do not significantly increase the permeability of the vesicles, do not cause them to flocculate and to melt and do not decrease the degree of encapsulation. Use is advantageously made of liposoluble active compounds which also constitute additives.

A particularly preferred form of lipid vesicles with an aqueous core includes vesicles comprising a lipid membrane obtained from a mixture of compound of formula (I) as defined above and of monosodium salt of hydrogenated tallow glutamate, in particular that sold under the name Amisoft HS-11® by the company Ajinomoto.

The aqueous phase of the dispersion in accordance with the invention can additionally contain a water-immiscible liquid that is dispersed in the aqueous phase by the lipid vesicles.

In this case, the compositions in accordance with the present invention are more particularly oil-in-water dispersions in which the lipid vesicles act as dispersant of the oil in the continuous aqueous phase.

The water-immiscible liquid, present in the form of a dispersion in the aqueous phase, can be chosen in particular from the group formed by:

animal or vegetable oils formed by esters of fatty acids and of polyols, in particular liquid triglycerides, for example sunflower, maize, soybean, cucumber, grapeseed, jojoba, sesame and hazelnut oils, fish oils, glycerol tricaprocaprylate or vegetable or animal oils of formula $R_9COOR_{10}$, in which formula $R_9$ represents the residue of a higher fatty acid having from 7 to 19 carbon atoms and $R_{10}$ represents a branched hydrocarbon-containing chain having from 3 to 20 carbon atoms, for example purcellin oil;

natural or synthetic essential oils, such as, for example, eucalyptus, lavandin, lavender, vetiver, litsea cubeba, lemon, sandlewood, rosemary, camomile, savory, nutmeg, cinnamon, hyssop, caraway, orange, geraniol, cade and bergamot oils;

hydrocarbons, such as hexadecane and liquid paraffin;

halogenated carbon-containing compounds, in particular fluorocarbons, such as fluoroamines, for example perfluorotributylamine, fluorinated hydrocarbons, for example perfluorodecahydronaphthalene, fluoroesters and fluoroethers;

silicones, for example polysiloxanes, polydimethylsiloxanes and fluorosilicones;

alcohol and inorganic acid esters; and ethers and polyethers.

The aqueous phase of the dispersion can also contain water-soluble cosmetic and/or dermopharmaceutical active compounds. The water-immiscible liquid can optionally contain a liposoluble active compound.

The aqueous phase of the dispersion can also contain adjuvants having neither a specific cosmetic activity nor a specific dermopharmaceutical activity but used for the formulation of the dispersion in the lotion, cream, milk or serum form. These adjuvants are taken in particular from the group formed by gelling agents, preservatives, colorants, opacifiers, fragrances, pigments, sunscreens and powders for cosmetic use. Mention may be made, among the gelling agents which can be used, of derivatives of algae, such as satiagum, natural gums, such as gum tragacanth, and synthetic polymers, in particular the mixtures of polycarboxyvinyl acids sold under the name "Carbopol" by the company Goodrich.

The compositions according to the invention find in particular an application as composition for topical use.

In particular, the compositions as defined above can be used as, or for the preparation of, products for caring for and/or making up the face, body and/or scalp. These products can be provided in the form of a dispersion, which is more or less thickened, gel, cream, milk or serum.

The invention also relates to the novel compounds of following formula (I'):

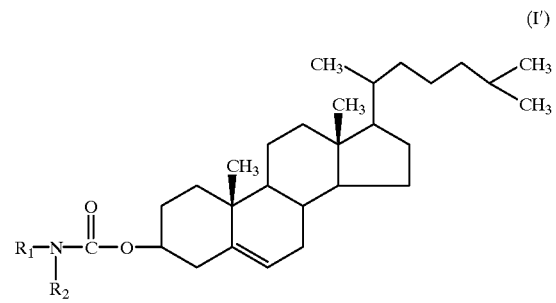

$R_1$ and $R_2$ having the same meaning as that indicated above for the compounds of formula (I), with the exception:

of N-cholesteryloxycarbonyl-N-methyl-D-glucamine ($R_1$ is methyl and $R_2$ is the —$(CH_2OH)_5$—$CH_2OH$ radical), and of the compounds in which:

either $R_1$ denotes a hydrogen atom and $R_2$ is a group chosen from: —CH(OH)—$CH_2$—$CH_2$—OH; —$CH_2$—CH(OH)—$CH_2$—OH; —CH($CH_2OH$)—$CH_2$—OH; —$CH_2$—CH(OH)—$CH_2$—$CH_2OH$ or $R_1$ denotes an alkyl radical chosen from the group formed by the methyl, ethyl, n-propyl, isopropyl, n-butyl and t-butyl radicals and $R_2$ denotes a group chosen from: —$CH_2$—CH(OH)—$CH_2$—OH; —CH($CH_2OH$)—$CH_2$—OH or $R_1$ and $R_2$ denote a —$CH_2$—$CH_2OH$ radical.

EXAMPLES

Having generally described this invention, a further understanding can be obtained by reference to certain specific examples which are provided herein for purposes of illustration only and are not intended to be limiting unless otherwise specified.

Example 1

Preparation of N-cholesteryloxycarbonyl-D-glucamine 100 g (0.552 mol) of D-glucamine were suspended, under an inert atmosphere, in 1 liter of N,N-dimethylacetamide and then 120 g (0.267 mol) of cholesteryl chloroformate were added in small amounts. The reaction mnixture was stirred for 2 hours and then poured into 10 liters of slightly acidic water. The precipitate formed was dried and 112 g (70% yield) of white powder were obtained. Melting point: 126° C. The $^1$H NMR spectrum is in accordance with the expected structure. Elemental analysis: $C_{34}H_{59}NO_7$

|  | % C | % H | % N | % O |
|---|---|---|---|---|
| Calculated | 68.77 | 10.01 | 2.36 | 18.86 |
| Found | 68.50 | 10.04 | 2.57 | 18.97 |

Example 2

Preparation of N-cholesteryloxycarbonyl-1,1-di(hydroxymethyl)ethylamine

The compound was synthesized according to the procedure of Example 1, using:

18.5 g (0.0412 mol) of cholesteryl chloroformate
9.5 g (0.09 mol) of 2-amino-2-methyl-1,3-propanediol
150 ml of N,N-dimethylacetamide
17.7 g (83% yield) of white powder were obtained. Melting point: 116° C. The $^1$H NMR spectrum is in accordance with the expected structure. Elemental analysis: $C_{31}H_{53}NO_4$

|  | % C | % H | % N | % O |
|---|---|---|---|---|
| Calculated | 74.23 | 10.71 | 2.71 | 12.36 |
| Found | 74.28 | 10.64 | 2.80 | 12.42 |

Example 3

Study of the Encapsulation Properties of the Vesicles

Vesicles with an aqueous core were prepared from lipids according to the invention, the membrane of which vesicles comprises 90% (weight/weight) of lipid according to the invention and 10% (weight/weight) of monosodium salt of hydrogenated tallow glutamate ("Amisoft HS-11" from the company Ajinomoto).

The encapsulation capacities of the vesicles and the maintenance of the encapsulation in the vesicles over time were measured.

The encapsulation capacity was determined by measuring the degree of swelling, expressed as microlitre/mg: it indicates the number of microlitres of aqueous phase which can be encapsulated in the vesicles by using 1 mg of lipids.

The maintenance of the encapsulation in the vesicles over time was determined by measuring the degree of leakage at 15 days and 30 days: it indicates the percentage of initially encapsulated phase which is found outside the vesicles.

The methods of determining the degree of swelling and the degree of leakage are well known to a person skilled in the art.

The study was carried out for two lipids according to the invention:

lipid 1: N-cholesteryloxycarbonyl-D-glucamine (compound of Example 1)

lipid 2: N-cholesteryloxycarbonyl-N-methyl-D-glucamine (compound described in Lange W. and Amundson M., J. of Pharmaceutical Sciences, Vol. 51, No. 11, 1962, the entire contents of which are hereby incorporated by reference).

The following results were obtained:

|  | Diameter (nm) | Swelling (μl/mg lipid) | Degree of leakage 15 days | Degree of leakage 30 days |
|---|---|---|---|---|
| Lipid 1 | 421 | 10 | 10% | 10% |
| Lipid 2 | 369 | 2.5 | 10% | 10% |

It was found that the two lipids according to the invention make it possible to prepare vesicles exhibiting good stability over time and a low degree of leakage, which remains constant over time. Furthermore, lipid I exhibits a good ability to be encapsulated which is better than that of lipid 2.

Example 4

Stability Study on the Vesicles

Vesicles with an aqueous core were prepared from the lipids 1 and 2 of Example 3 (lipids according to the invention) and their stability over time was studied.

A mixture of 90% (weight/weight) of lipid of formula (I) according to the invention and of 10% of monosodium salt of hydrogenated tallow glutamate ("Amisoft HS-11" from the company Ajinomoto) was added to a sufficient volume of water preheated to 80° C. After stirring for 30 minutes, the mixture was brought back to 60° C. and then homogenized using a high pressure homogenizer by passing at $5 \times 10^7$ Pa. Vesicles as a dispersion in water were thus obtained.

The sizes of the vesicles were measured after their formation (t=0):

lipid 1: 170 nm lipid 2: 182 nm

The dispersions obtained were then stored for 2 months at 4° C. and at 45° C. and the size of the vesicles was again measured. It was found that the size of the vesicles had not changed for the 2 lipids tested and under both temperature conditions. Furthermore, it was found that the polydispersity of the vesicles was constant and no recrystallization of product appeared.

These results obtained thus show that the lipids according to the invention exhibit a good ability to form stable vesicles.

Example 5

A moisturizing serum for the face was prepared which has the following composition:

| Phase A: | |
| --- | --- |
| N-cholesteryloxycarbonyl-N-methyl-D-glucamine (1) | 3.6 g |
| monosodium salt of hydrogenated tallow glutamate, sold under the name Amisoft HS-11 ® by Ajinomoto | 0.4 g |
| tocopherol acetate | 0.2 g |
| Phase B: | |
| distilled water | 50 g |
| glycerol | 5 g |
| Phase C: | |
| mixture of polycarboxyvinyl acid, sold under the name Carbopol 980 ® by the company Goodrich | 0.2 g |
| triethanolamine | 0.2 g |
| preservatives | q.s. |
| distilled water | q.s. for 100 g |

(1) this compound is described in Lange W. and Amundson M., J. of Pharmaceutical Sciences, vol. 51, No. 11, 1962.

Phase A was added with vigorous stirring to phase B, preheated to 80° C. After stirring for 30 minutes, it was found, using a microscope, that the lipids had fully hydrated, the lipids existing in the form of coarse vesicles.

The mixture thus obtained was brought back to 60° C. and then homogenized using a high pressure homogenizer by 3 passes at $5 \times 10^7$ Pa. Vesicles were then obtained having a mean size of the order of 200 nm.

Phase C was subsequently added at room temperature with stirring using a deflocculator (Rayneri).

An opalescent and fluid serum was thus obtained, which serum is easily applied to the face.

Example 6

A day cream was prepared which has the following composition:

| Phase A: | |
| --- | --- |
| N-cholesteryloxycarbonyl-D-glucamine (compound of Example 1) | 5.4 g |
| monosodium salt of hydrogenated tallow glutamate, sold under the name Amisoft HS-11 ® by Ajinomoto | 0.6 g |
| Phase B: | |
| distilled water | 40 g |
| glycerol | 3 g |
| Phase C: | |
| avocado oil | 6 g |
| volatile silicone oil | 6 g |
| liquid paraffin | 4 g |
| preservatives | 0.1 g |
| Phase D: | |
| mixture of polycarboxyvinyl acid, sold under the name Carbopol 980 ® by the company Goodrich | 0.4 g |
| triethanolamine | 0.4 g |
| distilled water | q.s. for 100 g |

The composition was prepared according to a procedure identical to that of Example 5.

Phase C was dispersed in the mixture of phases A and B and then homogenized. A dispersion of oil stabilized by the vesicles was thus obtained, the particle size of the oil dispersion being of the order of 250 nm. Finally, phase D was added in the same way as that of Example 5. A day cream was thus obtained, which cream is easily applied to the face.

Example 7

An anti-sun cream was prepared which has the following composition:

| | |
| --- | --- |
| N-cholesteryloxycarbonyl-D-glucamine | 2.7 g |
| monosodium salt of hydrogenated tallow glutamate, sold under the name Amisoft HS-11 ® by Ajinomoto | 0.3 g |
| tocopherol acetate | 0.3 g |
| Phase B: | |
| distilled water | 40 g |
| glycerol | 5 g |
| Phase C: | |
| octyl methoxycinnamate, sold under the name Parsol MCX ® by the company Givaudan | 15 g |
| volatile silicone oil | 6 g |
| Phase D: | |
| mixture of polycarboxyvinyl acid, sold under the name Carbopol 980 ® by the company Goodrich | 0.5 g |
| triethanolamine | 0.5 g |
| preservatives | q.s |
| distilled water | q.s. for 100 g |

Example 8

A scented milk was prepared which has the following composition:

| | |
| --- | --- |
| N-cholesteryloxycarbonyl-N-methyl-D-glucamine | 1.8 g |
| monosodium salt of hydrogenated tallow glutamate, sold under the name Amisoft HS-11 ® by Ajinomoto | 0.2 g |
| Phase B: | |
| distilled water | 15 g |
| glycerol | 3 g |
| Phase C: | |
| bergamot essential oil | 4 g |
| volatile silicone oil | 2 g |
| Phase D: | |
| mixture of polycarboxyvinyl acid, sold under the name Carbopol 980 ® by the company Goodrich | 0.2 g |

-continued

| | | |
|---|---|---|
| triethanolamine | 0.2 | g |
| preservatives | q.s | |
| distilled water | q.s. for 100 | g |

Having now fully described the invention, it will be apparent to one of ordinary skill in the art that many changes and modifications can be made thereto without departing from the spirit or scope of the invention as set forth herein.

This application is based on French Patent Application 9708801, filed Jul. 10, 1997, the entire contents of which are hereby incorporated by reference.

What is claimed as new and desired to be secured by Letters Patent of the United States is:

1. A composition, comprising:
an aqueous dispersion of vesicles comprising a lipid membrane, wherein said lipid membrane comprises at least one carbamate of following formula (I):

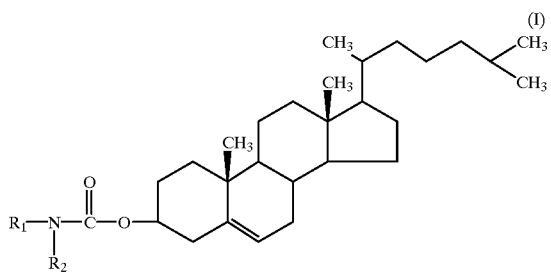

wherein $R_1$ is a hydrogen atom or an optionally hydroxylated, saturated or unsaturated, linear or branched alkyl radical having 1 to 6 carbon atoms, $R_2$ is an saturated or unsaturated, linear or branched alkyl radical having 3 to 6 carbon atoms, optionally hydroxylated, with the proviso that the $(R_1)(R_2)N$— group comprises at least two hydroxyl groups.

2. The composition according to claim 1, wherein the compound of formula (I) is selected from the group consisting of N-chlolesteryloxycarbonyl-N-methyl-D-glucamine, N-cholesteryloxycarbonyl-D-glucamine, N-cholesteryloxycarbonyl-1,1-di(hydroxymethyl) ethylamine or N-cholesteryloxycarbonyl-2,3-dihydroxypropylamine.

3. The composition according to claim 1, comprised of a dispersion of lipid vesicles with an aqueous core.

4. The composition according to claim 1, wherein said lipid membrane further comprises at least one ionic amphiphilic lipid and optionally at least one non-ionic amphiphilic lipid.

5. The composition according to claim 4, wherein a ratio by weight of the amount of carbamate of formula (I) to the amount of amphiphilic lipid is between 30/1 and 50/25.

6. The composition according to claim 3, wherein a ratio by weight of the amount of lipid membrane to the amount of aqueous phase of the dispersion is between 1/1000 and 300/1000.

7. The composition according to claim 3, wherein the lipid membrane of the vesicles with an aqueous core additionally comprises at least one additive selected from the group consisting of sterols, long-chain alcohols and dials, long-chain amines and their quaternary ammonium derivatives, and mixtures thereof.

8. The composition according to claim 7, wherein the additive is cholesterol.

9. The composition according to claim 1, comprised of a dispersion of lipid vesicles with an oily core.

10. The composition according to claim 9, wherein the vesicles with an oily core are comprised of dispersed oily globules individually coated with a monolamellar or oligolamellar layer comprising at least one carbamate of formula (I) and a surfactant selected from the group consisting of a lipophilic surfactant, a hydrophilic surfactant, and a mixture thereof.

11. The composition according to claim 10, wherein the monolamellar or oligolamellar layer additionally comprises either an ionic amphiphilic lipid or a fatty acid, in combination with a basic agent dissolved in the aqueous phase of the dispersion.

12. The composition according to claim 4, wherein the ionic amphiphilic lipid is selected from the group consisting of neutralized anionic lipids, amphoteric lipids, and alkyl-sulphonic derivatives, and mixtures thereof.

13. The composition according to claim 12, wherein the ionic amphiphilic lipid is selected from the group consisting of:

alkaline salts of dicetyl phosphate, of dimyristyl phosphate, of cholesterol sulphate or of cholesterol phosphate, salts of lipoamino acids, the sodium salt of phosphatidic acid, phospholipids, alkylsulphonic derivatives of formula:

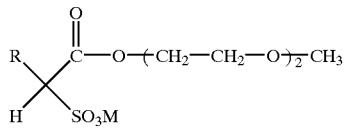

in which formula
R represents $C_{12}$–$C_{22}$ radicals taken as a mixture or separately, and M is an alkali metal,
and mixtures thereof.

14. The composition of claim 13, wherein R is selected from the group consisting of $C_{16}H_{33}$ and $C_{18}H_{37}$ radicals.

15. The composition according to claim 4, wherein the non-ionic amphiphilic lipid is selected from the group consisting of:

(1) linear or branched ethers of polyglycerol of formula (II)

$R^{10}O$—$_n$—H in which:
—$C_3H_5(OH)O$ is represented by the following structures, taken as a mixture or separately:

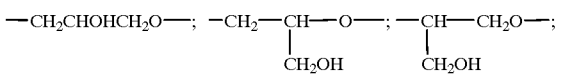

in which:
n is a mean statistical value of between 2 and 6;
$R^{10}$ represents:
(a) a linear or branched aliphatic chain comprising from 12 to 18 carbon atoms;
(b) an $R^{11}O$ residue, where $R^{11}$ is a linear or branched $C_{11}$–$C_{17}$ aliphatic radical;
(c) an $R^{12}$— residue, where:
$R^{12}$ can take the meaning (a) or (b) given for $R^{10}$;
$OC_2H_3(R^{13})$— is represented by the following structures, taken as a mixture or separately:

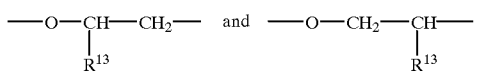

where $R^{13}$ takes the meaning (a) given for $R^{10}$;

(2) polyoxyethylenated fatty alcohols or polyoxyethylenated sterols;

(3) optionally polyoxyethylenated polyol esters;

(4) natural or synthetic glycolipids; and (5) oxyethylenated polyglycerol stearate; and mixtures thereof.

16. The composition according to claim 1, wherein the vesicles comprise at least one active compound having a cosmetic or dermopharmaceutical activity.

17. The composition according to claim 3, wherein the vesicles comprise a lipid membrane comprised of a mixture of the compound of formula (I) and a monosodium salt of hydrogenated tallow glutamate.

18. The composition according to claim 1, further comprising at least one water-immiscible liquid dispersed in the aqueous phase of the dispersion.

19. The composition according to claim 18, wherein the water-immiscible liquid is dispersed by the lipid vesicles.

20. The composition according to claim 1, wherein the aqueous phase of the dispersion additionally comprises a cosmetic, a dermopharmaccutically active compound, or an adjuvant selected from the group consisting of gelling agents, preservatives, colorants, opacifiers, fragrances, pigments, sunscreens, powders for cosmetic use, and mixtures thereof.

21. A topical composition for caring for or making up the face, body or scalp, comprising the composition according to claim 1.

22. A process for the non-therapeutic treatment of the skin or of the scalp, comprising applying the composition according to claim 1 to the skin or the scalp.

23. A method of dispersing a water-immiscible liquid in an aqueous phase, comprising dispersing a water-immiscible liquid in an aqueous phase with a compound of following formula (I'):

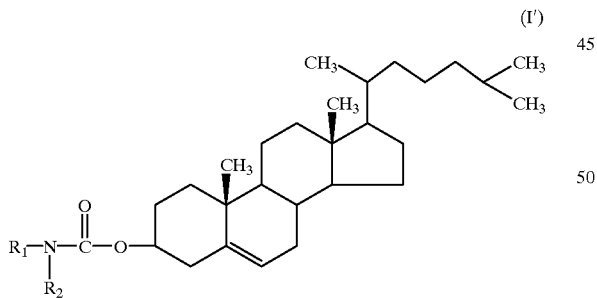

(I')

in which $R_1$ represents a hydrogen atom or an optionally hydroxylated, saturated or unsaturated, linear or branched alkyl radical having from 1 to 6 carbon atoms, $R_2$ represents a saturated or unsaturated, linear or branched alkyl radical having from 3 to 6 carbon atoms, optionally hydroxylated, with the proviso that the $(R_1)(R_2)$N-group comprises at least two hydroxyl groups, with the exception; of N-cholesteryloxycarbonyl-N-methyl-D-glucamine, of the compounds in which:

either $R_1$ represents a hydrogen atom and $R_2$ is: —CH(OH)—CH$_2$—CH$_2$—OH; —CH$_2$—CH(OH)—CH$_2$—OH; —CH(CH$_2$OH)—CH$_2$—OH; —CH$_2$—CH(OH)—CH$_2$—CH$_2$OH or $R_1$ represents an alkyl radical selected from the group consisting of methyl, ethyl, n-propyl, isopropyl, n-butyl and t-butyl radical and $R_2$ is: —CH$_2$—CH(OH)—CH$_2$—OH; —CH(CH$_2$OH)—CH$_2$—OH;

or $R_1$ $R_2$ represent a —CH$_2$—CH$_2$—CH$_2$OH radical.

24. A method of preparing lipid vesicles, comprising dispersing a compound of following formula (I'):

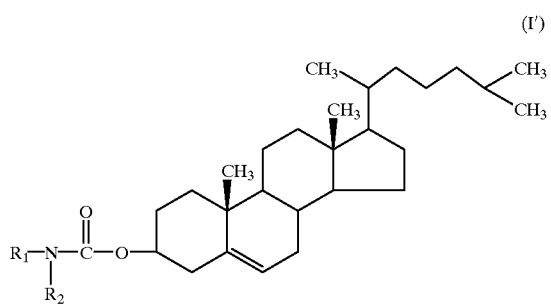

(I')

in which $R_1$ represents a hydrogen atom or an optionally hydroxylated, saturated or unsaturated, linear or branched alkyl radical having from 1 to 6 atoms, $R_2$ represents a saturated or unsaturated, linear or branched alkyl radical having from 3 to 6 carbon atoms, optionally hydroxylated, with the proviso that the $(R_1)(R_2)$N-group comprises at least two hydroxyl groups, with the exception: of N-chloesteryloxycarbonyl-N-methyl-D-glucamine, of the compounds in which: p1 either $R_1$ represents a hydrogen atom and $R_2$ is: —CH(OH)—CH$_2$—CH$_2$—OH; —CH$_2$—CH(OH)—CH$_2$—OH; —CH(CH$_2$OH)—CH$_2$—OH; —CH$_2$—CH(OH)—CH$_2$—CH$_2$OH or $R_1$ represents an alkyl radical selected from the group consisting of methyl, ethyl, n-propyl, isopropyl, n-butyl and t-butyl radicals and $R_2$ is: —CH$_2$—CH(OH)—CH$_2$—OH; —CH(CH$_2$OH)—CH$_2$—OH;

$R_1$ and $R_2$ represents a —CH$_2$—CH$_2$OH radical, in an aqueous phase.

25. An aqueous dispersion composition, comprising a compound of following formula (I'):

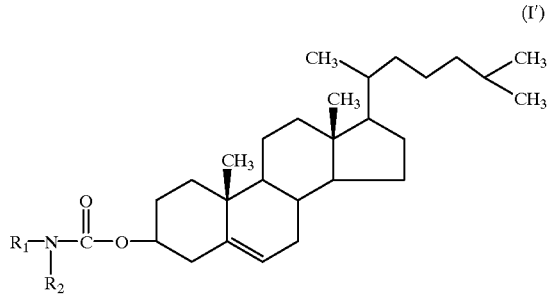

(I')

in which $R_1$ represents a hydrogen atom or an optionally hydroxylated, saturated or unsaturated, linear or branched alkyl radical having from 1 to 6 carbon atoms, $R_2$ represents an saturated or unsaturated, linear or branched alkyl radical having from 3 to 6 carbon atoms, optionally hydroxylated, with the proviso that the $(R_1)(R_2)$N-group comprises at least two hydroxyl groups, with the exception: of N-cholesteryloxycarbonyl-N-methyl-D-glucamine, of the compounds in which:

either $R_1$ represents a hydrogen atom and $R_2$ is: —CH(OH)—CH$_2$—CH$_2$—OH; —CH$_2$—CH(OH)—CH$_2$—OH; —CH(CH$_2$OH)—CH$_2$—OH; —CH$_2$—CH(OH)—CH$_2$—CH$_2$OH or $R_1$ represents an alkyl radical selected from the group consisting of methyl, ethyl, n-propyl, isopropyl, n-butyl and t-butyl radicals and $R_2$ is: —CH$_2$—CH(OH)—CH$_2$—OH; —CH(CH$_2$OH)—CH$_2$—OH;

or $R_1$ and $R_2$ represent a —CH$_2$—CH$_2$OH radical, in a vesicular lipid membrane.

26. A method of dispersing a water-immiscible liquid, comprising dispersing a water-immiscible liquid in the composition according to claim 1.

\* \* \* \* \*

UNITED STATES PATENT AND TRADEMARK OFFICE
CERTIFICATE OF CORRECTION

PATENT NO. : 6,130,213
DATED : October 10, 2000
INVENTOR(S) : Michel Philippe et al.

It is certified that error appears in the above-identified patent and that said Letters Patent is hereby corrected as shown below:

<u>Column 16,</u>
Line 32, after -- which: -- delete "p1".

Signed and Sealed this

Twelfth Day of March, 2002

Attest:

JAMES E. ROGAN
*Attesting Officer*  *Director of the United States Patent and Trademark Office*